US005916876A

United States Patent [19]
Heavner et al.

[11] Patent Number: 5,916,876
[45] Date of Patent: Jun. 29, 1999

[54] PEPTIDE INHIBITORS OF LEUKOCYTE ADHESION

[75] Inventors: George A. Heavner, Malvern, Pa.; Leon A. Epps, Baltimore, Md.

[73] Assignee: Centocor, Inc., Malvern, Pa.

[21] Appl. No.: 08/361,517

[22] Filed: Dec. 22, 1994

Related U.S. Application Data

[63] Continuation-in-part of application No. 07/941,652, Sep. 8, 1992, abandoned.

[51] Int. Cl.⁶ .............................. A61K 38/00; C07K 5/00; C07K 7/00
[52] U.S. Cl. .............................. 514/14; 514/15; 530/326; 530/327; 530/328
[58] Field of Search .................................... 530/326, 327, 530/328; 514/14, 15

[56] References Cited

U.S. PATENT DOCUMENTS

| | | | |
|---|---|---|---|
| 3,625,214 | 12/1971 | Higuchi | 424/424 |
| 4,789,734 | 12/1988 | Pierschbacher | 530/395 |
| 4,906,474 | 3/1990 | Langer et al. | 514/772.3 |
| 4,925,673 | 5/1990 | Steiner et al. | 424/455 |
| 5,081,034 | 1/1992 | Bavilacqua | 435/252.33 |
| 5,116,964 | 5/1992 | Capon et al. | 536/27 |
| 5,192,746 | 3/1993 | Lobl et al. | 514/11 |
| 5,198,424 | 3/1993 | McEver | 514/13 |
| 5,227,369 | 7/1993 | Rosen et al. | 514/23 |

FOREIGN PATENT DOCUMENTS

| | | |
|---|---|---|
| WO 91/07993 | 6/1991 | WIPO . |
| WO 91/19502 | 12/1991 | WIPO . |
| WO 92/19501 | 12/1991 | WIPO . |
| WO 91/01718 | 2/1992 | WIPO . |
| WO 92/02527 | 2/1992 | WIPO . |
| WO 94/02162 | 3/1994 | WIPO . |

OTHER PUBLICATIONS

Aruffo, A., et al., *Proc. Natl. Acad. Sci. USA*, 89, 2292–2296 (1992).
Bevilacqua, et al., in *Science* 243, 1160–1165 (1989).
Bevilacqua et al., *Proc.Natl.Acad.Sci.USA* 84: 9238–9242 (1987.
Geng, et al., *Nature* 343, 757–760 (1990).
Gregoriadis, G., Chapter 14, "Liposomes", *Drug Carriers in Biology and Medicine*, pp. 287–341 (Academic Press, 1979).
Hamburger and McEver, *Blood* 75:550–554 (1990).
Hattori, et al., *J. Biol. Chem.* 264: 7768–7771 (1989).
Issekutz, et al., *Lab. Invest.* 49: 716 (1983).
Johnston, et al., in *Cell* 56, 1033–1044 (Mar. 24 1989).
Larsen, et al., in *Cell* 59, 305–312 (Oct. 1989).
Lasky, et al., *Cell* 56, 1045–1055 (1989) (mouse).
Ley, et al., *Blood* 73, 1324–1330 (1989).
McEver, et al. *J. Clin. Invest.* 84: 92–99 (1989).
McEver and Martin, *J. Biol. Chem.* 259: 9799–9804 (1984).
McEver, et al., *Blood* 70(5) Suppl. 1:355a, Abstract No. 1274 (1987).
Merrifield in *J.Amer.Chem.Soc.*, 85, 2149–2154 (1963).
Moore, et al., *J. Cell Biol.* 112:491–499 (1991).
Muller–Eberhard, H.J., *Ann. Rev. Biochem.* 57: 321–347 (1988).
Romson et al., *Circulation* 67: 1016–1023 (1983).
Tedder, et al., *J. Exp. Med.* 170, 123–133 (1989).
Yednock and Rosen, *Advances in Immunology*, vol. 44, F.I. Dixon, ed., 313–378 (Academic Press, New York 1989).
Abbot et al., *Arthritis and Rheumatism*, vol. 35, No. 4, 401–406, 1992.
Ager et al., *International Immunology*, vol. 2, No. 10, 921–928, 1990.
Albelda, S.M., *American Journal of Respir. Cell and Molecular Biology*, vol. 4, 195–203, 1991.
Albelda et al., *The Faseb Journal*, vol. 4, 2868–2880, 1990.
Aruffo et al., *Cell*, vol. 67, 35–44, 1991.
Ball et al., *The Journal of the American Chemical Society*, vol. 114, 5449–5451, 1992.
Bennett, J. S., *Seminars in Hematology*, vol. 27, No. 2, 186–204, 1990.
Berg et al., *Biochemical and Biophysical Research Communications*, vol. 184, No. 2, 1048–1055, 1992.
Berg E., et al., *The Journal of Biological Chemistry*, vol. 266, No. 23, 14869–14872, 1991.
Berg M., et al., *Blood*, vol. 76, No. 11, 2381–2388, 1990.
Bevilacqua et al., *Cell*, vol. 67, 233, 1991.
Bradley et al., *The Journal of Immunology*, vol., 148, No. 2, 324–331, 1992.
Brandley et al., *Cell*, vol. 63, 861–863, 1990.
Brown et al., *Journal of Cell Biology* vol. 111, No.6, 2785–2794 (1990).
Bührer et al., *Scandinavian Journal of Immunology*, vol. 35, 107–120, 1992.
Camerini et al. *Nature*, vol. 342, 78–82, 1989.
Carmody et al., *Hybridoma*, vol. 9, No. 6, 631–641, 1990.
Celi et al., *Procedures of the Society of Experimental and Biological Medicine*, vol. 198, No. 2, 703–709, 1991.
Corral et al., *Biochemical and Biophysical Research Communications*, vol. 172, No. 3, 1349–1356, 1990.
Damle et al., *European Journal of Immunology*, vol. 22, 1789–1793, 1992.
de Bruijne–Admiraal et al., *Blood*, vol. 80,No. 1, 134–142, 1992.
Dejana et al., *Laboratory Investigation*, vol. 66, No. 3, 324–330, 1992.
Disdier et al., *Molecular Biology of the Cell*, vol. 3, 309–321, 1992.
Dunlop et al., *Journal of Experimental Medicine*, vol. 175, 1147–1150, 1992.

(List continued on next page.)

*Primary Examiner*—Avis M. Davenport
*Attorney, Agent, or Firm*—Woodcock Washburn Kurtz Makciewicz & Norris, LLP

[57] ABSTRACT

The present invention provides novel peptides derived from portions of the sequence of amino acids 42–48 of P-selectin. The invention also provides pharmaceutical compositions comprising the peptides of the invention, and diagnostic and therapeutic methods utilizing the peptides and pharmaceutical compositions of the invention.

23 Claims, 1 Drawing Sheet

OTHER PUBLICATIONS

Edgington, S.M., *Bio/Technology*, vol. 10, 383–389, 1992.
Erban et al., *The Journal of Biological Chemistry*, vol. 267, No. 4, 2451–2458, 1992.
Feizi, T., *journal unknown*, 84–86, 1991 Elsevier Science Publishers Ltd. (UK).
Fisher et al., *Applied Cardiopulmonary Pathophysiology*, vol. 4, 175–189, 1991.
Foxall et al., *The Journal of Cell Biology*, vol. 117, No. 4, 895–902, 1992.
Furie, B. et al., *Current Studies in Hematology Blood Transf.*, vol. 58, 32–36, 1991.
Furie, M. et al., *The Journal of Immunology*, vol. 148, No. 8, 2395–2404, 1992.
Gamble et al., *Science*. vol. 249, 414–416, 1990.
Geng et al., *The Journal of Biological Chemistry*, vol. 266, No. 33, 22313–22319, 1991.
Groves et al., *British Journal of Dermatology*, vol. 124, 117–123, 1991.
Hakkert et al., *Blood*, vol. 78, No. 10, 2721–2726, 1991.
Hamann et al., *European Journal of Immunology*, vol. 21, 2925–2929, 1991.
Handa et al., *Biochemical and Biophysical Research Communications*, vol. 181, No. 3, 1223–1230, 1991.
Handa et al., *Biochemistry*, vol. 30, 11682–11686, 1991.
Harrison, F. L., *Journal of Cell Science* vol. 100, 9–14, 1991.
Huang et al., *Journal of Clinical Investigation*, vol. 88, 1778–1783, 1991.
Israels et al., *Blood*, vol. 80, No. 1, 143–152, 1992.
James et al., *Immunology Research*, vol. 10, 282–292, 1991.
Johnston et al., *The Journal of Biological Chemistry*, vol. 265, No.34, 21381–21385, 1990.
Jutila, M.A., *APMIS*, vol. 100, 191–201,1992.
Jutila et al. *The Journal of Immunology*, vol. 143, No. 10, 3318–3324, 1989.
Kansas, G. S., *APMIS*, vol. 100, 287–293, 1992.
Karlsson, K. A., *TiPS*, vol. 12, 265–272, 1991.
Kitagawa et al., *Biochemical and Biophysical Research Communications*, vol. 178, No. 3, 1429–1436, 1991.
Knapp et al., *Current Opinion in Immunology*, vol. 2, 884–891, 1990.
Koedam et al., *The Journal of Cell Biology*, vol. 116, No. 3, 617–625, 1992.
Kojima et al., *Biochemical and Biophysical Research Communications*, vol. 182, No. 3, 1288–1295, 1992.
Kuijpers et al., *The Journal of Immunology*, vol. 147, No. 4, 1369–1376, 1991.
Larkin et al., *The Journal of Biological Chemistry*, vol. 267, No. 19, 13661–13668, 1992.
Larsen et al., *Cell*, vol. 63, 467–474,1990.
Lasky et al., *Cell*, vol. 69, 927–938, 1992.
Lawrence et al., *Cell*, vol. 65, 859–873, 1991.
Leeuwenberg et al., *Clinical Experiments in Immunology*, vol. 81, 496–500, 1990.
Leeuwenberg et al., *European Journal of Immunology*, vol. 21, 3057–3059, 1991.
Leeuwenberg et al., *Scandinavian Journal of Immunology*, vol. 35, 335–341, 1992.
Lin, Y.–C. et al., *The Journal of the American Chemical Society*, vol. 114, 5452–5454, 1992.
Lobb et al., *The Journal of Immunology*, vol. 147, No. 1, 124–129,1991.
Lorant et al., *The Journal of Cell Biology*, vol. 115, No. 1, 223–234, 1991.
Lowe et al., *Cell*, vol. 63, 475–484, 1990.
Lowe et al., *Biochemical Society Transactions*, vol. 19, No. 3, 649–653, 1991.
Majuri et al., *Biochemical and Biophysical Research Communications*. vol. 183, No. 3, 1376–1382, 1992.
May et al., *Biochemical and Biophysical Research Communications*, vol. 183, No. 3, 1062–1069, 1992.
McEver, R. P., *Journal of Cellular Biochemistry*, vol. 45, 156–161, 1991.
McEver, R.P., *Thrombosis and Haemostasis*, vol. 65, No. 3, 223–228, 1990.
McEver, R. P., *Thrombosis and Haemostasis*, vol. 66, No. 1, 80–87, 1991.
McEver, R.P., *TCM* vol. 1, No. 4, 152–156, 1991.
Metzelaar et al., *Virchows Archives B Cell Pathology*, vol. 61, 269–277, 1991.
Montefort et al., *Respiratory Medicine*, vol. 85, 91–99, 1991.
Mulligan et al., *Journal of Clinical Investigation*, vol. 88, 1396–1406, 1991.
Norton et al., *Clinical Experimental Immunology*, vol. 87, 231–236, 1992.
Ord et al., *The Journal of Biological Chemistry*, vol. 265, No. 14, 7760–7767, 1990.
Osborn et al., *Cell*, vol. 62, 3–6,1990.
Parish et al., *Biochemical Society Transactions*, vol. 20, No.2, 295–297, 1992.
Parmentier et al., *Blood*, vol. 77, No. 8, 1734–1739, 1991.
Parmentier et al., Platelet Immunology *Fundamental and Clinical Aspects*, vol. 206, 63–73, 1991.
Parmentier et al., *Immunology Today*, vol. 11, No. 7, 1990.
Patarroyo, M., *Clinical Immunology and Immunopathology*, vol. 60, 333–348, 1991.
Patel et al., *Journal of Cell Biology*, vol. 112, No. 4, 749–759, 1991.
Picker et al., *Cell*, vol. 66, 921–933, 1991.
Pigott et al., *The Journal of Immunology*, vol. 147, No. 1, 130–135, 1991.
Pober et al., *Laboratory Investigation*, vol. 64, No. 3, 301, 1991.
Pober et al., *Transplantation*, vol. 50, No. 4, 537–544, 1990.
Postigo et al., *Journal of Clinical Investigation*, vol. 89, 1445–1452, 1992.
Rinder et al., *Blood*, vol. 78, No. 7, 1730–1737, 1991.
Rinder et al., *Blood*, vol. 78, No. 7, 1760–1769, 1991.
Ryan et al., *Current Opinion in Immunology*, vol. 4, 33–37, 1992.
Shimizu et al., *The Journal of Cell Biology*, vol. 113, No. 5, 1203–1212, 1991.
Shimizu et al., *Nature*, vol. 349, 799–802, 1991.
Shipp et al., *Blood*, vol. 78, No. 7, 1834–1841, 1991.
Siegelman et al., *Cell*, vol. 61, 611–622, 1990.
Skinner et al., *The Journal of Biological Chemistry*, vol. 266, No. 9, 5371–5374, 1991.
Smith et al., *Cancer and Metastasis Reviews*, vol. 10, 61–78, 1991.
Smith, C. W., *American Journal of Respiratory Cell Molecular Biology*, vol. 2, 487–489, 1990.
Spertini et al., *Journal of Experimental Medicine*, vol. 175, 1789–1792, 1992.
Spertini et al., *The Journal of Immunology*, vol. 147. No. 8, 2565–2573, 1991.
Springer, T.A., *Nature* vol. 346, 425–434,1990.
Springer et al., *Nature*, vol. 349, 196–197, 1991.

Stoolman, L. M., *Selectins (LEC–CAMs): Lectin–Like Receptors Involved in Lymphocyte Recirculation and Leukocyte Recruitment, Cell Surface Carbohydrates and Cell Development*, Fukuda, M., Ph.D., Ed., CRC Press, 71–98.

Swiedler, S. J., *Glycobiology*, vol. 1, No. 3, 237–241, 1991.

Takada et al., *Biochemical and Biophysical Research Communications*, vol. 179, No. 2, 713–719, 1991.

Todoroki et al., *Biochemical and Biophysical Research Communications*, vol. 179, No. 2, 756–761, 1991.

Toothill et al., *The Journal of Immunology*, vol. 145, No. 1, 283–291, 1990.

True et al., *The Journal of Cell Biology*, vol. 111, No. 6, Pt. 1, 2757–2764, 1990.

Tyrrell et al., *Procedures of the National Academy of Science. USA*, vol. 88, 10372–10376, 1991.

Vadas et al., *Biochemical Pharmacology*, vol. 40, No. 8, 1683–1687, 1990.

Volpes et al., *Hepatology*, vol. 15, No. 2, 269–275, 1992.

Walcheck et al., *European Journal of Immunology*, vol. 22, 469–476, 1992.

Watson, M. et al., *Journal of Experimental Medicine*, vol. 172, 263–272, 1990.

Watson, S. et al., *The Journal of Cell Biology*, vol. 115, No. 1, 235–243, 1991.

Watson, S. et al., *Nature*, vol. 349, 164–166,1991.

Wautier et al., *Biorheology*. vol. 27, 425–432, 1990.

Winocour et al., *Comparative Biochemistry and Physiology*, vol. 102A, No. 2, 265–271, 1992.

Wong et al., *Procedures of the National Academy of Science. USA*, vol. 88, 2397–2401,1991.

Yong et al., *Blood Reviews*, vol.4, 211–225, 1990.

Aruffo, A. et al., "Granule Membrane Protein 140 (GMP140) Binds to Carcinomas and Carcinoma–Derived Cell Lines", *PNAS USA* 1992, 89, 2292–2296.

Heavner, G. et al., "Peptides from Multiple Regions of the Lectin Domain of P–Selectin Inhibiting Neutrophil Adhesion", *Int. J. Peptide Protein Res.* 1993, 42, 484–489.

Merrifield, R.B., "Solid Phase Peptide Synthesis. I. The Synthesis of a Tetrapeptide", *J. Am. Chem. Soc.* 1963, 85, 2149–2154.

Romson, J. et al., "Reduction of the Extent of Ischemic Myocardial Injury by Neutrophil Depletion in the Dog", *Circulation* 1983, 67(5), 1016–1023.

Johnston et al, *Cell*, vol.56, pp. 1033–1044, Mar. 24, 1989.

Geng et al., *Nature*, vol. 343, pp. 757–760, Feb. 22, 1990.

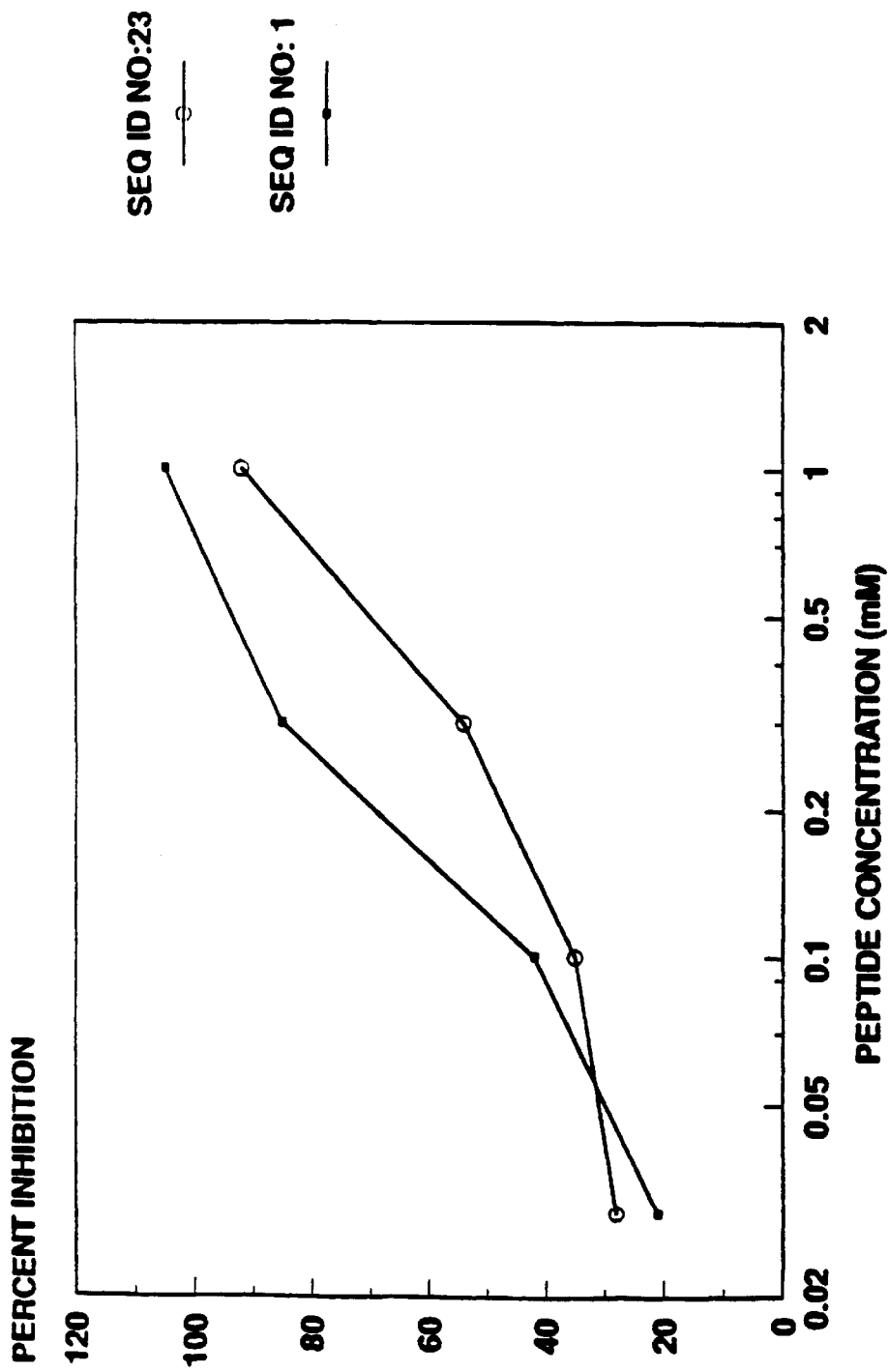

PEPTIDE INHIBITORS OF LEUKOCYTE ADHESION

RELATED APPLICATIONS

This application is a continuation-in-part of U.S. Ser. No. 07/941,652, filed Sep. 8, 1992 now abandoned.

BACKGROUND OF THE INVENTION

This invention relates to peptides which inhibit binding of selectins such as P-selectin, E-selectin and L-selectin.

The adherence of platelets and leukocytes to vascular surfaces is a critical component of the inflammatory response and is part of a complex series of reactions involving the simultaneous and interrelated activation of the complement, coagulation, and immune systems.

The complement proteins collectively play a leading role in the immune system, both in the identification and in the removal of foreign substances and immune complexes, as reviewed by Muller-Eberhard, H. J., *Ann. Rev. Biochem.* 57: 321–347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Leukocyte adherence to vascular endothelium is a key initial step in migration of leukocytes to tissues in response to microbial invasion. Although a class of inducible leukocyte receptors, the CD11–CD18 molecules, are thought to have some role in adherence to endothelium, mechanisms of equal or even greater importance for leukocyte adherence appear to be due to inducible changes in the endothelium itself.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. In response to vascular injury, platelets are known to adhere to subendothelial surfaces, become activated, and support coagulation. Platelets and other cells may also play an important role in the recruitment of leukocytes into the wound in order to contain microbial invasion.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial surface receptors. The slower cytokine-inducible endothelial adhesion for leukocytes is mediated, at least in part, by E-selectin that is synthesized by endothelial cells after exposure to cytokines and then transported to the cell surface, where it binds neutrophils. The isolation, characterization and cloning of E-selectin or ELAM-1 is reviewed by Bevilacqua, et al., in *Science* 243, 1160–1165 (1989). L-selectin, a peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of the protein is reviewed by Lasky, et al., *Cell* 56, 1045–1055 (1989) (mouse) and Tedder, et al., *J. Exp. Med.* 170, 123–133 (1989).

P-selectin, also known as GMP-140 (granule membrane protein 140), or PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). P-selectin was first purified from human platelets by McEver and Martin, *J. Biol. Chem.* 259: 9799–9804 (1984). The protein is present in alpha granules of resting platelets but is rapidly redistributed to the plasma membrane following platelet activation, as reported by Stenberg, et al., *J. Cell Bio.* 101, 880–886 (1985). The presence of P-selectin in endothelial cells and its biosynthesis by these cells was reported by McEver, et al., *Blood* 70(5) Suppl. 1:355a, Abstract No. 1274 (1987). In endothelial cells, P-selectin is found in storage granules known as the Weibel-Palade bodies. (McEver, et al. *J. Clin. Invest.* 84: 92–99 (1989) and Hattori, et al., *J. Biol. Chem.* 264: 7768–7771 (1989)). P-selectin (called GMP-140 or PADGEM) has also been reported to mediate the interaction of activated platelets with neutrophils and monocytes by Larsen, et al., in *Cell* 59, 305–312 (October 1989) and Hamburger and McEver, *Blood* 75: 550–554 (1990).

The cDNA-derived amino acid sequence, reported by Johnston, et al., in *Cell* 56, 1033–1044 (Mar. 24, 1989), and in U.S. Ser. No. 07/320,408 filed Mar. 8, 1989, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound P-selectin is presented within seconds on the cell surface. The rapid redistribution of P-selectin to the surface of platelets and endothelial cells as a result of activation suggested that this glycoprotein could play an important role at sites of inflammation or vascular disruption.

This important role has been confirmed by the observation that P-selectin is a receptor for neutrophils (Geng et al., *Nature* 343:757–760 (1990); Hamburger and McEver, *Blood* 75:550–554 (1990)), monocytes (Larsen, et al. *Cell* 59:305–312 (1989)); Moore, et al., *J. Cell Biol.* 112:491–499 (1991)), and perhaps a subset of lymphocytes (Moore, et al. *J. Cell Biol.* 112:491–499 (1991)). Thus, GMP-140 can serve as a receptor for leukocytes following its rapid mobilization to the surfaces of platelets and endothelial cells stimulated with agonists such as thrombin. This role in leukocyte recruitment may be important in hemostatic and inflammatory processes in both physiologic and pathologic states.

Peptides derived from P-selectin are described in U.S. Ser. No. 07/554,199 entitled "Functionally Active Selectin-Derived Peptides" filed Jul. 17, 1990 by Rodger P. McEver that are useful in diagnostics and in modulating the hemostatic and inflammatory responses in a patient wherein a therapeutically effective amount of a peptide capable of blocking leukocyte recognition of P-selectin is administered to the patient. U.S. Ser. No. 07/554,199 filed Jul. 17, 1990 also discloses that peptide sequences within the lectin domain of P-selectin, having homology with the lectin domains of other proteins, especially E-selectin and the L-selectin, selectively inhibit neutrophil adhesion to purified P-selectin, and can therefore be used in diagnostic assays of patients and diseases characterized by altered binding by these molecules, in screening assays for compounds altering this binding, and in clinical applications to inhibit or modulate interactions of leukocytes with platelets or endothelial cells involving coagulation and/or inflammatory processes.

E-selectin, L-selectin, and P-selectin have been termed "selecting", based on their related structure and function. E-selectin is not present in unstimulated endothelium. However, when endothelium is exposed to cytokines such as tumor necrosis factor of interleukin-1, the gene for E-selectin is transcribed, producing RNA which in turn is translated into protein. The result is that E-selectin is expressed on the surface of endothelial cells one to four hours after exposure to cytokines, as reported by Bevilacqua et al., *Proc.Natl.Acad.Sci.USA* 84: 9238–9242 (1987) (in contrast to P-selectin, which is stored in granules and presented on the cell surface within seconds after activation). E-selectin has been shown to mediate the adherence of neutrophils to cytokine-treated endothelium and thus appears to be important in allowing leukocytes to migrate across cytokine-stimulated endothelium into tissues. The cDNA-derived primary structure of E-selectin indicates that it contains a "lectin" domain, an EGF domain, and six (instead of the nine in P-selectin) repeats similar to those of complement-regulatory proteins, a transmembrane domain, and a short cytoplasmic tail. There is extensive sequence homology between P-selectin and E-selectin throughout both proteins, but the similarity is particularly striking in the lectin and EGF domains.

Homing receptors are lymphocyte surface structures that allow lymphocytes to bind to specialized endothelial cells in lymphatic tissues, termed high endothelial cells or high endothelial venules (reviewed by Yednock and Rose, *Advances in Immunology,* vol. 44, F. I. Dixon, ed., 313–378 (Academic Press, New York 1989). This binding allows lymphocytes to migrate across the endothelium into the lymphatic tissues where they are exposed to processed antigens. The lymphocytes then re-enter the blood through the lymphatic system. L-selectin, a lymphocyte homing receptor, contains a lectin domain, an EGF domain, two complement-binding repeats, a transmembrane domain, and a short cytoplasmic tail. L-selectin also shares extensive sequence homology with P-selectin, particularly in the lectin and EGF domains.

Based on a comparison of the lectin domains between P-selectin, E-selectin, and L-selectin, it may be possible to select those peptides inhibiting binding of neutrophils to P-selectin which will inhibit binding of E-selectin, L-selectin, and other homologous selecting, to components of the inflammatory process, or, conversely, which will inhibit only P-selectin binding.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49:716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

It is preferable to develop peptides which can be prepared synthetically, having activity at least equal to, or greater than, the peptides derived from the protein itself.

It is therefore an object of the present invention to provide peptides interacting with cells recognized by selecting, including P-selectin, E-selectin, and L-selectin.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to P-selectin, E-selectin and L-selectin.

SUMMARY OF THE INVENTION

It has now been found that peptides of the selectin 36–50 sequence are effective in inhibiting the adhesion of leukocytes, especially neutrophils, to selecting.

This invention relates to novel peptides having a formula selected from Formulas I, II and III:

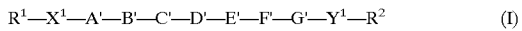
$$R^1—X^1—A'—B'—C'—D'—E'—F'—G'—Y^1—R^2 \qquad (I)$$

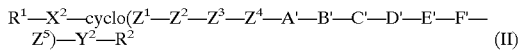
$$R^1—X^2—\text{cyclo}(Z^1—Z^2—Z^3—Z^4—A'—B'—C'—D'—E'—F'—Z^5)—Y^2—R^2 \qquad (II)$$

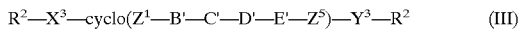
$$R^2—X^3—\text{cyclo}(Z^1—B'—C'—D'—E'—Z^5)—Y^3—R^2 \qquad (III)$$

or a pharmaceutically acceptable acid- or base-addition salt thereof, wherein:

A' is D- or L-leucine, D- or threoine, or D- or L-glutamine;

B' is D- or L-proline, D- or L-serine, D- or L-alanine, D- or L-valine, D- or L-isoleucine, D- or L-leucine, 2-aminobutyric acid, or null (signifying no amino acid);

C' is D- or L-tyrosine, D- or L-proline, D- or L-arginine, or D- or L-alanine;

D' is D- or L-tyrosine, D- or L-phenylalanine, D- or L-serine or glycine;

E' is D- or L-serine, D- or L-threonine, or D- or L-proline;

F' is D- or L-serine, D- or L-tyrosine, D- or L-alanine, or D- or L-threonine;

G' is D- or L-tyrosine, or D- or L-alanine;

$X^1$, $X^2$ and $X^3$ are each, independently, a linear chain of from 0 to 6 amino acids;

$Y^1$, $Y^2$ and $Y^3$ are each, independently, a linear chain of from 0 to 3 amino acids;

$Z^1$ and $Z^5$ are independently selected from the group consisting of D- or L-cysteine, D- or L-homocysteine, D- or L-aspartic acid, D- or L-glutamic acid, D- or L-lysine, D- or L-3-amino propionic acid, D- or L-4-amino butyric acid, and D- or L-5-amino valeric acid, provided that (a) when one of $Z^1$ and $Z^5$ is a cysteine or homo-cysteine, the other is also independently a cysteine or homo-cysteine; (b) when one of $Z^1$ and $Z^5$ is an aminodicarboxylic acid, then the other is a diaminodicarboxylic acid;

$Z^2$ is D- or L-asparagine;

$Z^3$ is D- or L-lysine;

$Z^4$ is D- or L-valine, D- or L-proline, D- or L-serine, D- or L-aspartic acid, or glycine;

$R^1$ is H (signifying a free-terminal amino group), formyl, lower alkyl, aryl, lower alkanoyl, aroyl, alkyloxycarbonyl, aryloxycarbonyl or desamino (signifying no alpha amino group on the N-terminal amino acid); and $R^2$ is H (signifying descarboxy where the α carboxyl group in the C-terminal amino acid is absent), $OR^3$, or $NR^4 R^5$;

$R^3$ is H (signifying a free carboxylic acid on a C-terminal carboxyl group) or lower alkyl or aryl; and $R^4$ and $R^5$ are each selected independently from H, lower alkyl, and aryl, or taken together are a methylene chain of 4–8 methylene groups (—$(CH_2)_n$— where n=4 to 8); provided that, when X'—A'—B'—C'—D'—E'—F'—G'—Y' is DYLNKVLPYYSSYYW, then $R^2$ is $NH_2$.

Peptides of the invention have as their core region portions of the 42–48 amino acid sequences of the selectins, with residue 1 defined as the N-terminus of the mature proteins after the cleavage of the signal peptides.

The peptides of Formulas II and III are cyclic by virtue of the formation of a disulfide bond between cysteine residues or an amide bond between side chain groups of diaminocarboxylic acid and an aminodicarboxylic acid. The general techniques for the formation of this bond are described by G. Barany and R. B. Merrifield in *The Peptides Analysis, Synthesis, Biology*, (Academic Press, Inc., 1979), as well as in other reference works known to those skilled in the art.

Tests indicate that peptides of the invention inhibit the binding of neutrophils to P-selectin in concentrations of peptide ranging from about 1 to about 1500 μm. Tests also indicate that alterations within the core sequence, including the addition or deletion of amino acids, do not result in loss of biological activity.

This invention relates not only to the novel peptides of Formulas I, II and III, but also to pharmaceutical compositions comprising them, to diagnostic and therapeutic methods utilizing them, and to methods of preparing them.

BRIEF DESCRIPTION OF THE DRAWINGS

FIG. 1 shows the ability of the peptides of Example 1, Glu-Tyr-Leu-Asn-Ser-Ile-Leu-Ser-Tyr-Ser-Pro-Ser-Tyr-Tyr-Trp-$NH_2$ (SEQ ID NO:23), and the peptide of Example II, Asp-Tyr-Leu-Asn-Lys-Val-Leu-Pro-Tyr-Tyr-Ser-Ser-Tyr-Tyr-Val-$NH_2$ (SEQ ID NO:1), to inhibit the binding of human neutrophils to human P-selectin in a dose-dependent manner.

DETAILED DESCRIPTION OF THE INVENTION

Preferred peptides of this invention are those of Formula I as previously defined, wherein $X^1$ is selected from a group consisting of:

Glu-Tyr-Leu-Asn-Ser-Ile,

Asp-Tyr-Leu-Asn-Lys-$X^4$, where $X^4$ is selected from the group consisting of Val, Pro, Gly, Ser and Asp;

Tyr-Leu-Asn-Lys-Val,

Leu-Asn-Lys-Val,

Asn-Lys-Val,

Asp-Val,

Lys-Val,

Asn-Thr,

Val, Lys or null (signifying no amino acid), wherein each of the above-designated amino acids may be a D- or L- amino acid.

Additional preferred peptides of this invention are those of Formula II where $X^2$ is selected from the group consisting of Asp-Tyr, Tyr, and null (signifying no amino acid), wherein each of the amino acids may be a D- or L-amino acid.

Still addition preferred peptides of the invention are those of Formula III where $X^3$ is selected from the group consisting of Asp-Tyr-Leu-Asn-Lys-Val Tyr-Leu-Asn-Lys-Val Leu-Asn-Lys-Val Asn-Lys-Val, and Lys-Val, wherein each of the amino acids may be a D- or L- amino acid.

Also preferred are peptides having Formula I as previously defined, wherein $Y^1$ is selected from a group consisting of Tyr, Tyr-Val, Tyr-Trp, $X^5$-$X^6$-Val-, where $X^5$ and $X^6$ are each independently an aromatic or hydrophobic amino acid; and null (signifying no amino acid), where each of the amino acids may be a D- or L- amino acid.

Additional preferred peptides are those of Formula II where $Y^2$ is selected from the group consisting of Tyr-Val, Tyr, and null (signifying no amino acid), wherein each of the amino acids may be a D- or L- amino acid.

Still additional preferred peptides are those of Formula III where $Y^3$ is selected from the group consisting of Tyr-Tyr-Val, Tyr-Tyr, Tyr, and null (signifying no amino acid), wherein each of the amino acids may be a D- or L-amino acid.

Representative examples of specifically preferred peptides include the following "Preferred Peptides" (SEQ ID NOS:1–42):

(SEQ ID NO: 1)  Asp—Tyr—Leu—Asn—Lys—Val—Leu—Pro—Tyr—Tyr—Ser—Ser—Tyr—Tyr—Val-NH₂;
(SEQ ID NO: 2)  Tyr—Leu—Asn—Lys—Val—Leu—Pro—Tyr—Tyr—Ser—Ser—Tyr—Tyr—Val-NH₂;
(SEQ ID NO: 3)  Leu—Asn—Lys—Val—Leu—Pro—Tyr—Tyr—Ser—Ser—Tyr—Tyr—Val-NH₂;
(SEQ ID NO: 4)  Asn—Lys—Val—Leu—Pro—Tyr—Tyr—Ser—Ser—Tyr—Tyr—Val-NH₂;
(SEQ ID NO: 5)  Lys—Val—Leu—Pro—Tyr—Tyr—Ser—Ser—Tyr—Tyr—Val-NH₂;
(SEQ ID NO: 6)  Asp—Tyr—Leu—Asn—Lys—Val—Leu—Pro—Tyr—Tyr—Ser—Ser—Tyr—Tyr-NH₂;
(SEQ ID NO: 7)  Val—Leu—Pro—Tyr—Tyr—Ser—Ser—Tyr—Tyr-NH₂;
(SEQ ID NO: 8)  Leu—Pro—Tyr—Tyr—Ser—Ser—Tyr—Tyr-NH₂;
(SEQ ID NO: 9)  Lys—Thr—Leu—Pro—Phe—Ser—Ser—Tyr—Tyr-NH₂;
(SEQ ID NO: 10) Val—Leu—Pro—Tyr—Tyr—Ser—Ser—Tyr—Tyr—Val-NH₂;
(SEQ ID NO: 11) Val—Leu—Pro—Tyr—Tyr—Ser—Ser—Tyr-NH₂;
(SEQ ID NO: 12) Lys—Val—Leu—Ala—Tyr—Tyr—Ser—Ser—Tyr—Tyr-NH₂;
(SEQ ID NO: 13) Lys—Val—Leu—Pro—Ala—Tyr—Ser—Ser—Tyr—Tyr-NH₂;
(SEQ ID NO: 14) Lys—Val—Leu—Pro—Tyr—Tyr—Ser—Ala—Tyr—Tyr-NH₂;
(SEQ ID NO: 15) Lys—Val—Leu—Pro—Tyr—Tyr—Ser—Ser—Ala—Tyr-NH₂;
(SEQ ID NO: 16) Lys—Val—Leu—Pro—Tyr—Tyr—Ser—Thr—Tyr—Tyr-NH₂;
(SEQ ID NO: 17) Lys—Val—Leu—Pro—Tyr—Tyr—Thr—Ser—Tyr—Tyr-NH₂;
(SEQ ID NO: 18) Asp—Val—Leu—Pro—Tyr—Tyr—Ser—Ser—Tyr—Tyr-NH₂;
(SEQ ID NO: 19) Lys—Val—Leu—Pro—Tyr—Gly—Ser—Ser—Tyr—Tyr-NH₂;
(SEQ ID NO: 20) Lys—Val—Leu—Pro—Arg—Tyr—Ser—Ser—Tyr—Tyr-NH₂;
(SEQ ID NO: 21) Asn—Thr—Leu—Pro—Tyr—Ser—Pro—Tyr—Tyr—Tyr-NH₂;
(SEQ ID NO: 22) Lys—Val—Gln—Pro—Tyr—Tyr—Ser—Ser—Tyr—Tyr-NH₂;
(SEQ ID NO: 23) Glu—Tyr—Leu—Asn—Ser—Ile—Leu—Ser—Tyr—Ser—Pro—Ser—Tyr—Tyr—Trp-NH₂;
(SEQ ID NO: 24) Asp—Tyr-cyclo(Cys—Asn—Lys—Val—Leu—Pro—Tyr—Tyr—Ser—Ser—Cys)—Tyr—Val-NH₂;
(SEQ ID NO: 25) Tyr-cyclo(Cys—Asn—Lys—Val—Leu—Pro—Tyr—Tyr—Ser—Ser—Cys)—Tyr—Val-NH₂;
(SEQ ID NO: 26) Asp—Tyr-cyclo(Cys—Asn—Lys—Val—Leu—Pro—Tyr—Tyr—Ser—Ser—Cys)—Tyr-NH₂;
(SEQ ID NO: 27) Asp—Tyr-cyclo(Cys—Asn—Lys—Val—Leu—Pro—Tyr—Tyr—Ser—Ser—Cys)-NH₂;
(SEQ ID NO: 28) Tyr-cyclo(Cys—Asn—Lys—Val—Leu—Pro—Tyr—Tyr—Ser—Ser—Cys)—Tyr-NH₂;
(SEQ ID NO: 29) cyclo(Cys—Asn—Lys—Val—Leu—Pro—Tyr—Tyr—Ser—Ser—Cys)—Tyr—Val-NH₂;
(SEQ ID NO: 30) cyclo(Cys—Asn—Lys—Val—Leu—Pro—Tyr—Tyr—Ser—Ser—Cys)—Tyr-NH₂;
(SEQ ID NO: 31) cyclo(Cys—Asn—Lys—Val—Leu—Pro—Tyr—Tyr—Ser—Ser—Cys)-NH₂;
(SEQ ID NO: 32) Asp—Tyr—Leu—Asn—Lys—Val-cyclo(Cys—Pro—Tyr—Tyr—Ser—Cys)—Tyr—Tyr—Val-NH₂;
(SEQ ID NO: 33) Tyr—Leu—Asn—Lys—Val-cyclo(Cys—Pro—Tyr—Tyr—Ser—Cys)—Tyr—Tyr—Val-NH₂;
(SEQ ID NO: 34) Leu—Asn—Lys—Val-cyclo(Cys—Pro—Tyr—Tyr—Ser—Cys)—Tyr—Tyr—Val-NH₂;
(SEQ ID NO: 35) Asn—Lys—Val-cyclo(Cys—Pro—Tyr—Tyr—Ser—Cys)—Tyr—Tyr—Val-NH₂;
(SEQ ID NO: 36) Lys—Val-cyclo(Cys—Pro—Tyr—Tyr—Ser—Cys)—Tyr—Tyr—Val-NH₂;
(SEQ ID NO: 37) Asp—Tyr—Leu—Asn—Val-cyclo(Cys—Pro—Tyr—Tyr—Ser—Cys)—Tyr—Tyr-NH₂;
(SEQ ID NO: 38) Asp—Tyr—Leu—Asn—Val-cyclo(Cys—Pro—Tyr—Tyr—Ser—Cys)—Tyr-NH₂;
(SEQ ID NO: 39) Asp—Tyr—Leu—Asn—Lys—Val-cyclo(Cys—Pro—Tyr—Tyr—Ser—Cys)-NH₂;
(SEQ ID NO: 40) Tyr—Leu—Asn—Lys—Val-cyclo(Cys—Pro—Tyr—Tyr—Ser—Cys)—Tyr—Tyr-NH₂;
(SEQ ID NO: 41) Leu—Asn—Lys—Val-cyclo(Cys—Pro—Tyr—Tyr—Ser—Cys)—Tyr—Tyr-NH₂;
(SEQ ID NO: 42) Leu—Asn—Lys—Val-cyclo(Cys—Pro—Tyr—Tyr—Ser—Cys)—Tyr-NH₂.

Table I shows the ability of certain preferred peptides to inhibit binding of human neutrophils to human P-selectin at a peptide concentration of 300 μM.

TABLE I

| STRUCTURE | | % INHIBITION AT 0.3 μM PEPTIDE CONC. |
|---|---|---|
| DYLNKVLPYYSSYYV-NH₂ | (SEQ ID NO: 1) | 71 |
| YLNKVLPYYSSYYV-NH₂ | (SEQ ID NO: 2) | 101 |
| LNKVLPYYSSYYV-NH₂ | (SEQ ID NO: 3) | 100 |
| NKVLPYYSSYYV-NH₂ | (SEQ ID NO: 4) | 80 |
| KVLPYYSSYYV-NH₂ | (SEQ ID NO: 5) | 102 |
| DYLNKVLPYYSSYY-NH₂ | (SEQ ID NO: 6) | 61 |
| VLPYYSSYY-NH₂ | (SEQ ID NO: 7) | 11 |
| LPYYSSYY-NH₂ | (SEQ ID NO: 8) | 15 |
| KTLPFSSYY-NH₂ | (SEQ ID NO: 9) | 33 |
| VLPYYSSYYV-NH₂ | (SEQ ID NO: 10) | 66 |
| VLPYYSSY-NH₂ | (SEQ ID NO: 11) | 25 |
| KVLAYYSSYY-NH₂ | (SEQ ID NO: 12) | 68 |
| KVLPAYSSYY-NH₂ | (SEQ ID NO: 13) | 20 |
| KVLPYYSAYY-NH₂ | (SEQ ID NO: 14) | 18 |
| KVLPYYSSAY-NH₂ | (SEQ ID NO: 15) | 12 |
| KVLPYYSTYY-NH₂ | (SEQ ID NO: 16) | 22 |
| KVLPYYTSYY-NH₂ | (SEQ ID NO: 17) | 32 |
| DVLPYYSSYY-NH₂ | (SEQ ID NO: 18) | 57 |
| KVLPYGSSYY-NH₂ | (SEQ ID NO: 19) | 34 |
| KVLPRYSSYY-NH₂ | (SEQ ID NO: 20) | 19 |
| NTLPYSPYYY-NH₂ | (SEQ ID NO: 21) | 39 |
| KVQPYYSSY Y-NH₂ | (SEQ ID NO: 22) | 29 |
| EYLNSILSYSPSYYW-NH₂ | (SEQ ID NO: 23) | 54 |

As used herein, the term "alkyl" includes branched, straight-chain, and cyclic saturated hydrocarbons. The term "lower alkyl" means an alkyl having from one to six carbon atoms, such as methyl, ethyl, propyl, isopropyl, butyl, isobutyl, t-butyl, pentyl, isopentyl, neopentyl, cyclopentyl-methyl and hexyl. The term "alkanoyl" means

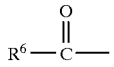

wherein R⁶ is a alkyl group.

The term "aroyl" means

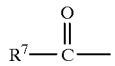

wherein R⁷ is an aryl group. The term "aryl" means an aromatic or heteroaromatic structure having between one and three rings, which may or may not be ring fused structures, and are optionally substituted with halogens, carbons, or other heteroatoms such as nitrogen (N), sulfur (S), phosphorus (P), and boron (B).

The term alkoxycarbonyl means

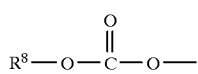

wherein $R^8$ is a lower alkyl group.

The term aryloxycarbonyl means

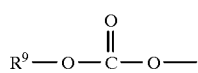

wherein $R^9$ is an aryl and arylmethyl group.

Halogen refers to fluorine, chlorine, bromine or iodine.

The term "terminal α-amino group of X" refers to the α-amino group of the N-terminal amino acid of X.

The peptides of the invention can be used in the form of the free peptide or a pharmaceutically acceptable salt. Amine salts can be prepared by treating the peptide with an acid according to known methods. Suitable acids include inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid.

Carboxylic acid groups in the peptide can be converted to a salt by treating the peptide with a base according to known methods. Suitable bases include inorganic bases such as sodium hydroxide, ammonium hydroxide, and potassium hydroxide, and organic bases such as mono-, di-, and tri-alkyl and aryl amines (e.g., triethylamine, diisopropylamine, methylamine, and dimethylamine and optionally substituted mono-, di, and tri-ethanolamines.

As referred to herein, the amino acid components of the peptides and certain materials used in their preparation are identified by abbreviations for convenience. These abbreviations are as follows:

| Amino Acid Abbreviations | | |
|---|---|---|
| L-alanine | Ala | A |
| D-alanine | D-Ala | a |
| L-arginine | Arg | R |
| D-arginine | D-Arg | r |
| D-asparagine | D-Asn | N |
| L-asparagine | Asn | n |
| L-aspartic acid | Asp | D |
| D-aspartic acid | D-Asp | d |
| L-cysteine | Cys | C |
| D-cysteine | D-Cys | c |
| L-glutamic acid | Glu | E |
| D-glutamic acid | D-Glu | e |
| L-glutamine | Gln | Q |
| D-glutamine | D-Gln | q |
| glycine | Gly | G |
| L-histidine | His | H |
| D-histidine | D-His | h |
| L-isolelucine | Ile | I |
| D-isolelucine | D-Ile | i |
| L-leucine | Leu | L |
| D-leucine | D-Leu | l |
| L-lysine | Lys | K |
| D-lysine | D-Lys | k |
| L-phenylalanine | Phe | F |
| D-phenylalanine | D-Phe | f |
| L-proline | Pro | P |
| D-proline | D-Pro | p |
| L-pyroglutamic acid | pGlu | |
| D-pyroglutamic acid | DpGlu | |
| L-serine | Ser | S |
| D-serine | D-Ser | s |
| L-threonine | Thr | T |
| D-threonine | D-Thr | t |
| L-tyrosine | Tyr | Y |
| D-tyrosine | D-Tyr | y |
| L-tryptophan | Trp | W |
| D-tryptophan | D-Trp | w |
| L-valine | Val | V |
| D-valine | D-Val | v |
| L-alloisolucine | Allo | |
| D-alloisolucine | D-Allo | |

| Reagents | Abbreviations |
|---|---|
| Trifluoroacetic acid | TFA |
| Methylene chloride | $CH_2Cl_2$ |
| N,N-Diisopropylethylamine | DIEA |
| N-Methylpyrrolidone | NMP |
| 1-Hydroxybenzotriazole | HOBT |
| Dimethylsulfoxide | DMSO |
| Acetic anhydride | $Ac_2O$ |
| Diisopropylcarbodiimide | DIC |

Amino acids preceded by L- or D- refer, respectively, to the L- or D- enantiomer of the amino acid, whereas amino acids not preceded by L- or D- refer to the L- enantiomer.

The term "aromatic amino acid" as used herein means an amino acid containing, or substituted with, an aryl group. Aromatic amino acids include phenylalanine, tyrosine, tryptophan, histidine, and naphthylalanine.

The term "hyrophobic amino acid" as used herein means amino acids containing non-polar groups that tend to decrease water solubility. Hydrophobic amino acids include, but are not limited to, leucine, isoleucine, valine, phenylalanine, alanine and naphthylalanine.

Methods of Preparation of Peptides

The peptides can generally be prepared following known techniques, as described, for example, in the cited publications, the teachings of which are specifically incorporated herein. In a preferred method, the peptides are prepared following the solid-phase synthetic technique initially described by Merrifield in *J.Amer.Chem.Soc.*, 85, 2149–2154 (1963). Other techniques may be found, for example, in M. Bodanszky, et al, *Peptide Synthesis,* second edition, (John Wiley & Sons, 1976), as well as in other reference works known to those skilled in the art.

Appropriate protective groups usable in such syntheses and their abbreviations will be found in the above text, as well as in J. F. W. McOmie, *Protective Groups in Organic Chemistry,* (Plenum Press, New York, 1973). The common protective groups used herein are t-butyloxycarbonyl (Boc), fluorenylmethoxycarboyl (FMOC), benzyl (Bzl), tosyl (Tos), o-bromo-phenylmethoxycarbonyl (BrCBZ), phenyl-methoxycarbonyl (CBZ), 2-chloro-phenylmethoxycarbonyl (2-Cl-CBZ), 4-methoxy-2,3,6-trimethylbenzenesulfonyl (Mtr), trityl (Trt), formyl (CHO), and tertiary butyl (t-Bu).

General synthetic procedures for the synthesis of peptides of the invention by solid phase methodology are as follows:

|   |   | REPETITIONS | TIME |
|---|---|---|---|
| A. General Synthetic Procedures For Solid Phase Peptide Synthesis Using $N^\alpha$-Boc Protection | | | |
| 1. | 25% TFA in $CH_2Cl_2$ | 1 | 3 min. |
| 2. | 50% TFA in $CH_2Cl_2$ | 1 | 16 min. |
| 3. | $CH_2Cl_2$ | 5 | 3 min. |
| 4. | 5% DIEA in NMP | 2 | 4 min. |
| 5. | NMP | 6 | 5 min. |
| 6. | Coupling step | 1 | 57 min. |
|    | a. Preformed BOC-Amino Acid-HOBT active ester in NMP | | 37 min. |
|    | b. DMSO | | 16 min. |
|    | c. DIEA | | 5 min. |
| 7. | 10% $Ac_2O$, 5% DIEA in NMP | 1 | 9 min. |
| 8. | $CH_2Cl_2$ | 5 | 3 min. |
| B. General Synthetic Procedure For Solid Phase Peptide Synthesis Using $N^\alpha$-FMOC Protection | | | |
| 1. | 50% piperidine in NMP | 1 | 1 min. |
| 2. | 50% piperidine in NMP | 1 | 12 min. |
| 3. | NMP wash | 7 | 1 min. |
| 4. | Coupling | 2 | 30 min. |
|    | FMOC amino acid dissolved in HOBT/NMP followed by the addition of DIC (di-isopropylcarbodiamide) in NMP. | | |
| 5. | NMP wash. | 2 | 1 min. |

N-terminal acetylation on the deprotected $N^\alpha$-amino group of peptides synthesized using either Boc or FMOC strategies is accomplished with 10% $Ac_2O$ and 5% DIEA in NMP, followed by washing of the peptide resin with NMP and/or $CH_2Cl_2$.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein which can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

Peptides of the invention can also be prepared using solution methods, by either stepwise or fragment condensations. An appropriately alpha amino-protected amino acid is coupled to an appropriately alpha carboxyl protected amino acid (such protection may not be required depending on the coupling method chosen) using diimides, symmetrical or unsymmetrical anhydrides, BOP, or other coupling reagents or techniques known to those skilled in the art. These techniques may be either or enzymatic. The alpha amino and/or alpha carboxyl protecting groups are removed and the next suitably protected amino acid or block of amino acids are coupled to extend the growing peptide. Various combinations of protecting groups and of chemical and/or enzymatic techniques and assembly strategies can be used in each synthesis.

Methods of Preparation of Pharmaceutical Compositions

Pharmaceutical compositions of this invention comprise a pharmaceutically acceptable carrier or diluent and an effective quantity of one or more of the peptides of the invention or an acid or base salt thereof. The carrier or diluent may take a wide variety of forms depending on the form of preparation desired for administration, e.g., sublingual, rectal, nasal, oral, or parenteral.

In preparing the compositions in oral dosage form, any of the usual pharmaceutical media may be employed, for example, waters, oils, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate liquid carriers and suspending agents can be employed.

The peptides can also be administered locally at a wound or inflammatory site by topical application of a solution or cream.

Alternatively, the peptide may be administered in liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14, "Liposomes", *Drug Carriers in Biology and Medicine*, pp. 287–341 (Academic Press, 1979). Microspheres formed of polymers or proteins are well known to those skilled in the art, and can be tailored for passage through the gastrointestinal tract directly into the bloodstream. Alternatively, the peptide can be incorporated and the microspheres, or composite of microspheres, implanted for slow release over a period of time, ranging from days to months. See, for example, U.S. Pat. Nos. 4,906,474, 4,925,673 and 3,625,214.

The peptides are generally active when administered parenterally in amounts above about 1 μg/kg body weight. The peptides are generally active when administered parenterally in amounts above about 1 μg/kg body weight. Effective doses by other routes of administration are generally those which result in similar blood level to i.v. doses above about 1 μg/Kg. For treatment to prevent organ injury in cases involving reperfusion, the peptides may be administered parenterally in amounts from about 0.01 to about 10 mg/kg body weight. Generally, the same range of dosage amounts may be used in treatment of other diseases or of conditions where inflammation is to be reduced. This dosage will be dependent, in part, on whether one or more peptides are administered.

Methods for Demonstrating Binding

Peptides that are biologically active are those which inhibit binding of neutrophils, monocytes, subsets of lymphocytes or other cells to P-selectin, or which inhibit leukocyte adhesion to endothelium that is mediated by ELAM-1 and/or the homing receptor.

Peptides can be screened for their ability to inhibit adhesion to cells, for example, neutrophil adhesion to purified P-selectin immobilized on plastic wells, using the assay described by Geng, et al., *Nature* 343, 757–760 (1990).

Human neutrophils are isolated from heparinized whole blood by density gradient centrifugation on Mono-Poly resolving media, Flow Laboratories. Neutrophil suspensions are greater than 98% pure and greater than 95% viable by trypan blue exclusion. For adhesion assays, neutrophils are suspended at a concentration of $2\times10^6$ cells/mL in Hanks' balanced salt solution containing 1.26 mM $Ca^{2+}$ and 0.81 mM $Mg^{2+}$ (HBSS, Gibco) with g mg/mL human serum albumin (HBSS/HSA). Adhesion assays are conducted in triplicate in 96-well microtiter plates, Corning, incubated at 4° C. overnight with 50 microliters of various protein solutions.

P-selectin is isolated from human platelet lysates by immunoaffinity chromatography on antibody S12-Sepharose™ and ion-exchange chromatography on a Mono-Q™ column (FLPC, Pharmacia Fine Chemicals), as follows.

Outdated human platelet packs (100 units) obtained from a blood bank and stored at 4° C. are pooled, adjusted to 5 mM EDTA at pH 7.5, centrifuged at 4,000 rpm for 30 minutes in 1 liter bottles, then washed three times with 1 liter of 0.1 M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 mL screwtop tubes at –80° C. The frozen platelets are thawed and resuspended in 50 mL TBS, 5 mM benzamidine, 5 mM EDTA pH 7.5, 100 M leupeptin. The suspension is frozen and thawed two times in a dry ice-acetone bath using a 600 mL lyophilizing flask, then homogenized in a glass/teflon mortar and pestle and made 1 mM in DIFP. The NaCl concentration is adjusted to 0.5 M with a stock solution of 4 M NaCl. After stirring the suspension at 4° C., it is centrifuged in polycarbonate tubes at 33,000 rpm for 60 minutes at 4° C. The supernatant (0.5 M NaCl wash) is removed and saved; this supernatant contains the soluble form of P-selectin. Care is taken not to remove the top part of the pellet with the supernatant. The pellets are then homogenized in extraction buffer (TBS, 5 mM benzamidine, 5 mM EDTA, pH 7.5, 100 µM leupeptin, 2% Triton X-100). After centrifugation at 19,500 rpm for 25 minutes at 4° C., the supernatant is removed. The extraction procedure is repeated with the pellet and the supernatant is combined with the first supernatant. The combined extracts, which contain the membrane form of P-selectin, are adjusted to 0.5 M NaCl.

The soluble fraction (0.5 M NaCl wash) and the membrane extract (also adjusted to 0.5 M NaCl) are absorbed with separate pools of the monoclonal antibody S12 (directed to P-selectin) previously coupled to Affigel (Biorad) at 5 mg/mL for 2 hours at 4° C. After letting the resins settle, the supernatants are removed. The S12 Affigel containing bound GMP-140 is then loaded into a column and washed overnight at 4° C. with 400 mL of 0.5 M NaCl, 20 mM Tris pH 7.5, 0.01% Lubrol PX.

Bound P-selectin is eluted from the S12 Affigel with 100 mL of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2 M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

P-selectin is plated at 5 micrograms/mL and the control proteins: human serum albumin (Alb), platelet glycoprotein IIb/IIIa (IIb), von Willebrand factor (vWF), fibrinogen (FIB), thrombomodulin (TM), gelatin (GEL) or human serum (HS), are added at 50 micrograms/mL. All wells are blocked for 2 hours at 22° C. with 300 microliters HBSS containing 10 mg/mL HSA, then washed three times with HBSS containing 0.1% Tween-20 and once with HBSS. Cells ($2\times10^5$ per well) are added to the wells and incubated at 22° C. for 20 minutes. The wells are then filled with HBSS/HSA, sealed with acetate tape (Dynatech), and centrifuged inverted at 150 g for 5 minutes. After discarding nonadherent cells and supernates, the contents of each well are solubilized with 200 microliters 0.5% hexadecyltrimethylammonium bromide, Sigma, in 50 mM potassium phosphate, pH. 6.0, and assayed for myeloperoxidase activity, Ley, et al., *Blood* 73, 1324–1330 (1989). The number of cells bound is derived from a standard curve of myeloperoxidase activity versus numbers of cells. Under all assay conditions, the cells release less than 5% of total myeloperoxidase and lactate dehydrogenase. Inhibition is read as a lower percent adhesion, so that a value of 5% means that 95% of the specific adhesion was inhibited.

Clinical Applications

Since the selectins have several functions related to leukocyte adherence, inflammation, and coagulation, compounds which interfere with binding of P-selectin, E-selectin or L-selectin can be used to modulate these responses.

For example, the peptides can be used to competitively inhibit leukocyte adherence by competitively binding to P-selectin receptors on the surface of leukocytes. This kind of therapy would be particularly useful in acute situations where effective, but transient, inhibition of leukocyte-mediated inflammation is desirable. Chronic therapy by infusion of the peptides may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023 (1983)). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is now known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers. Recently, it was reported that P-selectin binds to tumor cells in a variety of human carcinoma tissue sections (colon, lung, and breast), and that P-selectin binds to the cell surface of a number of cell lines derived from various carcinomas, but not from melanomas. Aruggo, A., et al., *Proc. Natl. Acad. Sci. USA,* 89, 2292–2296 (1992). Aruggo et al. also reference earlier work suggesting that E-selectin might be involved in tumor metastasis by mediating the adhesion of a colon carcinoma cell line (HT-20) to activated endothelial cells in vitro. Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

The criteria for assessing response to therapeutic modalities employing these peptides, and, hence, effective dosages of the peptides of this invention for treatment, are dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response.

For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Diagnostic Reagents

The peptides can also be used for the detection of human disorders in which the ligands for the selectins might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the art. Inhibition of binding in the presence and absence of the lectin domain peptides can be used to detect defects or alterations in selectin binding. For selectins, such disorders would most likely be seen in patients with increased susceptibility to infections in which leukocytes would have defective binding to platelets and endothelium because of deficient leukocyte ligands for P-selectin.

The peptide is labeled radioactively, with a fluorescent tag, enzymatically, or with electron dense material such as gold for electron microscopy. The cells to be examined, usually leukocytes, are incubated with the labeled peptides and binding assessed by methods described above with antibodies to P-selectin, or by other methods known to those skilled in the art. If ligands for P-selectin are also found in the plasma, they can also be measured with standard ELISA or radioimmunoassay procedures, using labeled P-selectin-derived peptide instead of antibody as the detecting reagent.

The peptides can also be useful in in vivo imaging of concentrations of cells bearing selectin ligands. Cells expressing selectin ligands whose abnormally high local concentrations or presence within the body such as cancer cells, is indicative of a disorder can be imaged using labeled peptides. These labels may be either intrinsic or extrinsic to the structure of the specific selectin peptide and may include, but not be limited to high energy emitters such as $^{111}$In or non-radioactive dense atoms to enhance x-ray contrast.

The following examples are presented to illustrate, not limit, the invention. In the examples and throughout the specification, parts are by weight unless otherwise indicated.

EXAMPLE I: Glutamyl-tyrosyl-leucyl-asparaginyl-serinyl-isoleucyl-leucyl-serinyl-tyrosyl-serinyl-prolinyl-serinyl-tyrosyl-tyrosyl-tryptophan-amide (SEQ ID NO:23)

The peptide was prepared on an ABI Model 431A Peptide Synthesizer using Version 1.12 of the standard Boc software. 4-methyl benzhydrylamine resin (625 mg) was used in the synthesis. The final weight of the resin was 2.2 g.

The peptide was cleaved from the resin (2.2 g) using 22 mL of HF and 2.2 mL of anisole for 60 min at 0° C. The resin was washed with ether and the peptide extracted with 50% TFA/CH$_2$Cl$_2$ to give 1.65 g of crude peptide. The peptide was deformylated with 50 mL of 2% aqueous piperidine at 4° C. for 2 hours.

The crude peptide (1.60 g) was purified on a Vydac C-18 column (15μ, 5×25 cm) eluting with a 20–60% gradient of 80% acetonitrile in 0.1% TFA over 120 min at a flow rate of 15 mL per min. Fractions were collected, analyzed by HPLC and pure fractions pooled and lyophilized to give 49 mg. Amino acid analysis: Asx 1.01 (1), Glx 0.97 (1), Ile 0.98 (1), Leu 2.07 (2), Pro 1.01 (1), Ser 2.69 (4), Tyr 3.30 (4). FAB/MS: MH$^+$ 1884.9

EXAMPLE II: Aspartyl-tyrosyl-leucyl-asparginyl-lysyl-valyl-leucyl-prolyl-tyrosyl-tyrosyl-serinyl-serinyl-tyrosyl-tyrosyl-valine-amide (SEQ ID NO:1)

The peptide was prepared on an ABI Model 431A Peptide Synthesizer using Version 1.12 of the standard Boc software. 4-methyl benzhydrylamine resin (0.631 g, 0.5 mmol) was used in the synthesis. The final weight of the resin was 2.476 g.

The peptide was cleaved from the resin (2.389 g) using 24 mL of HF and 2.4 mL of anisole for 60 min at 0° C. The resin was washed with ether and the peptide extracted with a 1:1 solution of TFA/CH$_2$Cl$_2$ to give 1.044 g of crude peptide.

The crude peptide (944 mg) was purified on a Vydac C-18 column (15μ, 5.0×25 cm) by using four 230 mg injections, eluting with a 15–75% gradient of 80% acetonitrile in 0.1% TFA over 120 min at a flow rate of 15 per min. Fractions were collected, analyzed by HPLC and pure fractions pooled and lyophilized to give 238 mg. Amino acid analysis: Asx 2.03 (2), Leu 2.04 (2), Lys 0.97 (1), Pro 1.01 (1), Ser 1.46 (2), Tyr 4.64 (5), Val 1.97 (2). FAB/MS: MH$^+$ 1886

What is claimed is:

1. A peptide having a formula of:

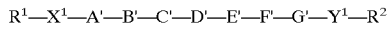

$$R^1—X^1—A'—B'—C'—D'—E'—F'—G'—Y^1—R^2$$

or a pharmaceutically acceptable acid- or base-addition salt thereof, wherein:

A' is D- or L-leucine, D- or L-threonine, or D- or L-glutamine;

B' is D- or L-proline, D- or L-serine, D- or L-alanine, D- or L-valine, D- or L-isoleucine, D- or L-leucine, 2-aminobutyric acid, or null (signifying no amino acid);

C' is D- or L-tyrosine, D- or L-proline, D- or L-arginine, or D- or L-alanine;

D' is D- or L-tyrosine, D- or L-phenylalanine, D- or L-serine or glycine;

E' is D- or L-serine, D- or L-threonine, or D- or L-proline;

F' is D- or L-serine, D- or L-tyrosine, D- or L-alanine, or D- or L-threonine;

G' is D- or L-tyrosine, or D- or L-alanine;

$X^1$ is independently, a linear chain of from 0 to 6 amino acids;

$Y^1$ is independently, a linear chain of from 0 to 3 amino acids;

$R^1$ is H (signifying a free-terminal amino group), formyl, lower alkyl, aryl, lower alkanoyl, aroyl, alkyloxycarbonyl, aryloxycarbonyl or desamino (signifying no alpha amino group on the N-terminal amino acid); and $R^2$ is H (signifying descarboxy where the α carboxyl group in the C-terminal amino acid is absent), $OR^3$, or $NR^4 R^5$;

$R^3$ is H (signifying a free carboxylic acid on a C-terminal carboxyl group) or lower alkyl or aryl; and $R^4$ and $R^5$ are each selected independently from H, lower alkyl, and aryl, or taken together are a methylene chain of 4–8 methylene groups ($—(CH_2)_n—$ where n=4 to 8);

provided that, when $X^1—A'—B'—C'—D'—E'—F'—G'—Y^1$ is DYLNKVLPYYSSYYW, then $R^2$ is $NH_2$.

2. A peptide of claim 1 wherein $X^1$ is selected from a group consisting of:

Glu-Tyr-Leu-Asn-Ser-Ile,
Asp-Tyr-Leu-Asn-Lys-X⁴, where X⁴ is selected from the group consisting of Val, Pro, Gly, Ser and Asp;
Tyr-Leu-Asn-Lys-Val,
Leu-Asn-Lys-Val,
Asn-Lys-Val,
Asp-Val,
Lys-Val,
Asn-Thr,
Val, Lys or null (signifying no amino acid),
wherein each of the above-designated amino acids may be a D- or L- amino acid.

3. A peptide of claim 1 wherein $Y^1$ is selected from a group consisting of Tyr, Tyr-Val, Tyr-Trp, $X^5$-$X^6$-Val-, where $X^5$ and $X^6$ are each independently an aromatic or hydrophobic amino acid; and null (signifying no amino acid), where each of the amino acids may be a D- or L- amino acid.

4. A peptide of claim 1 where $R^1$ is H and $R^2$ is $NH_2$.

5. A peptide of claim 1 wherein:
A' is D- or L-leucine, D- or L-threonine, or D- or L-glutamine;
B' is D- or L-proline, D- or L-serine, or D- or L-alanine;
C' is D- or L-tyrosine, D- or L-proline, D- or L-arginine, D- or L-alanine, or null (signifying no amino acid);
D' is D- or L-tyrosine, D- or L-phenylalanine, D- or L-serine or glycine;
E' is D- or L-serine, D- or L-threonine, or D- or L-proline;
F' is D- or L-serine, D- or L-tyrosine, D- or L-alanine, or D- or L-threonine;
G' is D- or L-tyrosine, or D- or L-alanine;
$X^1$ is a linear chain of from 0 to 6 amino acids;
$Y^1$ is a linear chain of from 0 to 2 amino acids;
$R^1$ is H (signifying a free-terminal amino group), formyl, lower alkyl, aryl, lower alkanoyl, aroyl, alkyloxycarbonyl, aryloxycarbonyl or desamino (signifying no alpha amino group on the N-terminal amino acid); and
$R^2$ is H (signifying descarboxy where the α carboxyl group in the C-terminal amino acid is absent), $OR^3$, or $NR^4 R^5$;
$R^3$ is H (signifying a free carboxylic acid on a C-terminal carboxyl group), lower alkyl or aryl;
$R^4$ and $R^5$ are each selected independently from H, lower alkyl, and aryl, or taken together are a methylene chain of 4–8 methylene groups (—$(CH_2)_n$— where n=4 to 8), provided that, when $X^1$—A'—B'—C'—D'—E'—F'—G'—$Y^1$ is DYLNKVLPYYSSYYW, then $R^2$ is $NH_2$.

6. A peptide of claim 5 wherein $X^1$ is selected from the group consisting of:
Glu-Tyr-Leu-Asn-Ser-Ile Asp-Tyr-Leu-Asn-Lys-Val,
Tyr-Leu-Asn-Lys-Val,
Leu-Asn-Lys-Val,
Asn-Lys-Val,
Asn-Thr,
Lys-Val,
Asp-Val
Val, Lys or null (signifying no amino acid).

7. A peptide of claim 5 wherein $Y^1$ is selected from a group consisting of Tyr, Tyr-Val, Tyr-Trp, or null (signifying no amino acid).

8. A peptide of claim 6 wherein $Y^1$ is selected from a group consisting of Tyr, Tyr-Val, Tyr-Trp, or null (signifying no amino acid).

9. A peptide of claim 5 wherein
A' is D- or L- leucine or D- or L-glutamine;
B' is D- or L- proline or D- or L-serine;
C' is D- or L-tyrosine, D- or L-alanine, D- or L-arginine, or null (signifying no amino acid);
D' is D- or L-tyrosine, D- or L-phenylalanine, D- or L-serine or glycine;
E' is D- or L-serine, D- or L-threonine or D- or L-proline;
F' is D- or L-serine, D- or L-threonine, D- or L-alanine or D- or L-tyrosine;
G' is D- or L-tyrosine or D- or L-alanine;
$X^1$ is a linear amino acid chain selected from the group consisting of Glu-Tyr-Leu-Asn-Ser-Ile, Asp-Tyr-Leu-Asn-Lys-Val, Tyr-Leu-Asn-Lys-Val, Leu-Asn-Lys-Val, Asn-Lys-Val, Asn-Thr, Lys-Val, Asp-Val, Lys-Thr, Val, and null (signifying no amino acid);
$Y^1$ is a linear amino acid chain selected from the group consisting of Tyr, Val, Tyr-Val, Tyr-Trp, and null (signifying no amino acid);
$R^1$ is H (signifying a free-terminal amino group), formyl, lower alkyl, aryl, lower alkanoyl, aroyl, alkyloxycarbonyl, aryloxycarbonyl or desamino (signifying no alpha amino group on the N-terminal amino acid);
$R^2$ is H (signifying descarboxy where the α-carboxyl group in the C-terminal amino acid is absent), $OR^3$, or $NR^4R^5$;
$R^3$ is H (signifying a free carboxylic acid on a C-terminal carboxyl group), lower alkyl or aryl;
$R^4$ and $R^5$ are each selected independently from H, lower alkyl, and aryl, or taken together are a methylene chain of 4–8 methylene groups (—$(CH_2)_n$— where n=4 to 8);
provided that, when $X^1$—A'—B'—C'—D'—E'—F'—G'—$Y^1$ is DYLNKVLPYYSSYYW, then $R^2$ is $NH_2$.

10. A peptide of claim 5 where $R^1$ is H and $R^2$ is $NH_2$.
11. A peptide of claim 9 where $R^1$ is H and $R^2$ is $NH_2$.
12. A peptide of claim 1 selected from the group consisting of:

| | |
|---|---|
| (SEQ ID NO: 1) | Asp—Tyr—Leu—Asn—Lys—Val—Leu—Pro—Tyr—Tyr—Ser—Ser—Tyr—Tyr—Val-NH₂; |
| (SEQ ID NO: 2) | Tyr—Leu—Asn—Lys—Val—Leu—Pro—Tyr—Tyr—Ser—Ser—Tyr—Tyr—Val-NH₂; |
| (SEQ ID NO: 3) | Leu—Asn—Lys—Val—Leu—Pro—Tyr—Tyr—Ser—Ser—Tyr—Tyr—Val-NH₂; |
| (SEQ ID NO: 4) | Asn—Lys—Val—Leu—Pro—Tyr—Tyr—Ser—Ser—Tyr—Tyr—Val-NH₂; |
| (SEQ ID NO: 5) | Lys—Val—Leu—Pro—Tyr—Tyr—Ser—Ser—Tyr—Tyr—Val-NH₂; |
| (SEQ ID NO: 6) | Asp—Tyr—Leu—Asn—Lys—Val—Leu—Pro—Tyr—Tyr—Ser—Ser—Tyr—Tyr-NH₂; |
| (SEQ ID NO: 7) | Val—Leu—Pro—Tyr—Tyr—Ser—Ser—Tyr—Tyr-NH₂; |
| (SEQ ID NO: 8) | Leu—Pro—Tyr—Tyr—Ser—Ser—Tyr—Tyr-NH₂; |
| (SEQ ID NO: 9) | Lys—Thr—Leu—Pro—Phe—Ser—Ser—Tyr—Tyr-NH₂; |
| (SEQ ID NO: 10) | Val—Leu—Pro—Tyr—Tyr—Ser—Ser—Tyr—Tyr—Val-NH₂; |

-continued (SEQ ID NO: 11) Val—Leu—Pro—Tyr—Tyr—Ser—Ser—Tyr-$NH_2$;
(SEQ ID NO: 12) Lys—Val—Leu—Ala—Tyr—Tyr—Ser—Ser—Tyr—Tyr-$NH_2$;
(SEQ ID NO: 13) Lys—Val—Leu—Pro—Ala—Tyr—Ser—Ser—Tyr—Tyr-$NH_2$;
(SEQ ID NO: 14) Lys—Val—Leu—Pro—Tyr—Tyr—Ser—Ala—Tyr—Tyr-$NH_2$;
(SEQ ID NO: 15) Lys—Val—Leu—Pro—Tyr—Tyr—Ser—Ser—Ala—Tyr-$NH_2$;
(SEQ ID NO: 16) Lys—Val—Leu—Pro—Tyr—Tyr—Ser—Thr—Tyr—Tyr-$NH_2$;
(SEQ ID NO: 17) Lys—Val—Leu—Pro—Tyr—Tyr—Thr—Ser—Tyr—Tyr-$NH_2$;
(SEQ ID NO: 18) Asp—Val—Leu—Pro—Tyr—Tyr—Ser—Ser—Tyr—Tyr-$NH_2$;
(SEQ ID NO: 19) Lys—Val—Leu—Pro—Tyr—Gly—Ser—Ser—Tyr—Tyr-$NH_2$;
(SEQ ID NO: 20) Lys—Val—Leu—Pro—Arg—Tyr—Ser—Ser—Tyr—Tyr-$NH_2$;
(SEQ ID NO: 21) Asn—Thr—Leu—Pro—Tyr—Ser—Pro—Tyr—Tyr—Tyr-$NH_2$;
(SEQ ID NO: 22) Lys—Val—Gln—Pro—Tyr—Tyr—Ser—Ser—Tyr—Tyr-$NH_2$;
(SEQ ID NO: 23) Glu—Tyr—Leu—Asn—Ser—Ile—Leu—Ser—Tyr—Ser—Pro—Ser—Tyr—Tyr—Trp-$NH_2$.

13. A pharmaceutical composition comprising at least one peptide of claim 1 in an amount effective to inhibit cellular adherence and a pharmaceutically acceptable carrier or diluent.

14. The pharmaceutical composition of claim 13 wherein said pharmaceutically acceptable carrier or diluent is acceptable for parenteral administration.

15. The pharmaceutical composition of claim 13 wherein said pharmaceutically acceptable carrier or diluent is acceptable for oral administration.

16. A peptide of claim 1 wherein each of A', B', C', D', E', F', and G' is an L-amino acid, and wherein $X^1$ and $Y^1$ comprise L-amino acids.

17. A peptide of claim 2 wherein each of A', B', C', D', E', F', and G' is an L-amino acid, and wherein $X^1$ and $Y^1$ comprise L-amino acids.

18. A peptide of claim 3 wherein each of A', B', C', D', E', F', and G' is an L-amino acid, and wherein $X^1$ and $Y^1$ comprise L-amino acids.

19. A peptide of claim 9 wherein each of A', B', C', D', E', F', and G' is an L-amino acid, and wherein $X^1$ and $Y^1$ comprise L-amino acids.

20. A peptide of claim 12 wherein each of A', B', C', D', E', F', and G' is an L-amino acid, and wherein $X^1$ and $Y^1$ comprise L-amino acids.

21. A peptide of claim 13 wherein each of A', B', C', D', E', F', and G' is an L-amino acid, and wherein $X^1$ and $Y^1$ comprise L-amino acids.

22. A peptide of claim 15 wherein each of A', B', C', D', E', F', and G' is an L-amino acid, and wherein $X^1$ and $Y^1$ comprise L-amino acids.

23. A pharmaceutical composition comprising at least one peptide of claim 21 in an amount effective to inhibit cellular adherence and a pharmaceutically acceptable carrier or diluent.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 15 amino acid residues
      (B) TYPE: amino acid
      (C) STRANDEDNESS:
      (D) TOPOLOGY: unknown (ii) MOLECULE TYPE:
      (A) DESCRIPTION: Amide terminated (xi) SEQUENCE DESCRIPTION: SEQ ID NO:1:

Asp Tyr Leu Asn Lys Val Leu Pro Tyr Tyr Ser Ser Tyr Tyr Val
 1         5               10            15

(2) INFORMATION FOR SEQ ID NO:2:

(i) SEQUENCE CHARACTERISTICS:
      (A) LENGTH: 14 amino acid residues
      (B) TYPE: amino acid
      (C) STRANDEDNESS:
      (D) TOPOLOGY: unknown (ii) MOLECULE TYPE:
      (A) DESCRIPTION: Amide terminated (xi) SEQUENCE DESCRIPTION: SEQ ID NO:2:

Tyr Leu Asn Lys Val Leu Pro Tyr Tyr Ser Ser Tyr Tyr Val
 1         5               10

(2) INFORMATION FOR SEQ ID NO:3:

(i) SEQUENCE CHARACTERISTICS:
      (A) LENGTH: 13 amino acid residues
      (B) TYPE: amino acid
      (C) STRANDEDNESS:
      (D) TOPOLOGY: unknown (ii) MOLECULE TYPE:
      (A) DESCRIPTION: Amide terminated (xi) SEQUENCE DESCRIPTION: SEQ ID NO:3:

Leu Asn Lys Val Leu Pro Tyr Tyr Ser Ser Tyr Tyr Val
 1         5               10

(2) INFORMATION FOR SEQ ID NO:4:

(i) SEQUENCE CHARACTERISTICS:

(A) LENGTH: 12 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:4:

Asn Lys Val Leu Pro Tyr Tyr Ser Ser Tyr Tyr Val
 1               5                  10

(2) INFORMATION FOR SEQ ID NO:5:

(i) SEQUENCE CHARACTERISTICS:
            (A) LENGTH: 11 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:5:

Lys Val Leu Pro Tyr Tyr Ser Ser Tyr Tyr Val
 1               5                  10

(2) INFORMATION FOR SEQ ID NO:6:

(i) SEQUENCE CHARACTERISTICS:
            (A) LENGTH: 14 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:6:

Asp Tyr Leu Asn Lys Val Leu Pro Tyr Tyr Ser Ser Tyr Tyr
 1               5                  10              14

(2) INFORMATION FOR SEQ ID NO:7:

(i) SEQUENCE CHARACTERISTICS:
            (A) LENGTH: 9 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:7:

Val Leu Pro Tyr Tyr Ser Ser Tyr Tyr
 1               5

(2) INFORMATION FOR SEQ ID NO:8:

(i) SEQUENCE CHARACTERISTICS:
            (A) LENGTH: 8 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:8:

Leu Pro Tyr Tyr Ser Ser Tyr Tyr
 1               5

(2) INFORMATION FOR SEQ ID NO:9:

(i) SEQUENCE CHARACTERISTICS:
        (A) LENGTH: 9 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:9:

```
Lys Thr Leu Pro Phe Ser Ser Tyr Tyr
  1               5
```

(2) INFORMATION FOR SEQ ID NO:10:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:10:

```
Val Leu Pro Tyr Tyr Ser Ser Tyr Tyr Val
  1               5                  10
```

(2) INFORMATION FOR SEQ ID NO:11:

(i) SEQUENCE CHARACTERISTICS:
        (A) LENGTH: 8 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:11:

```
Val Leu Pro Tyr Tyr Ser Ser Tyr
  1               5
```

(2) INFORMATION FOR SEQ ID NO:12:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:12:

```
Lys Val Leu Ala Tyr Tyr Ser Ser Tyr Tyr
  1               5                  10
```

(2) INFORMATION FOR SEQ ID NO:13:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:13:

Lys Val Leu Pro Ala Tyr Ser Ser Tyr Tyr
1               5                   10

(2) INFORMATION FOR SEQ ID NO:14:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:14:

Lys Val Leu Pro Tyr Tyr Ser Ala Tyr Tyr
1               5                   10

(2) INFORMATION FOR SEQ ID NO:15:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:15:

Lys Val Leu Pro Tyr Tyr Ser Ser Ala Tyr
1               5                   10

(2) INFORMATION FOR SEQ ID NO:16:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:16:

Lys Val Leu Pro Tyr Tyr Ser Thr Tyr Tyr
1               5                   10

(2) INFORMATION FOR SEQ ID NO:17:

(i) SEQUENCE CHARACTERISTICS:
        (A) LENGTH: 10 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:17:

Lys Val Leu Pro Tyr Tyr Thr Ser Tyr Tyr
1               5                   10

(2) INFORMATION FOR SEQ ID NO:18:

(i) SEQUENCE CHARACTERISTICS:
        (A) LENGTH: 10 amino acid residues
        (B) TYPE: amino acid (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:18:

Asp Val Leu Pro Tyr Tyr Ser Ser Tyr Tyr
 1               5                  10

(2) INFORMATION FOR SEQ ID NO:19:

(i) SEQUENCE CHARACTERISTICS:
            (A) LENGTH: 10 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:19:

Lys Val Leu Pro Tyr Gly Ser Ser Tyr Tyr
 1               5                  10

(2) INFORMATION FOR SEQ ID NO:20:

(i) SEQUENCE CHARACTERISTICS:
            (A) LENGTH: 10 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:20:

Lys Val Leu Pro Arg Tyr Ser Ser Tyr Tyr
 1               5                  10

(2) INFORMATION FOR SEQ ID NO:21:

(i) SEQUENCE CHARACTERISTICS:
            (A) LENGTH: 10 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:21:

Asn Thr Leu Pro Tyr Ser Pro Tyr Tyr Tyr
 1               5                  10

(2) INFORMATION FOR SEQ ID NO:22:

(i) SEQUENCE CHARACTERISTICS:
            (A) LENGTH: 10 amino acid residues
            (B) TYPE: amino acid
            (C) STRANDEDNESS:
            (D) TOPOLOGY: unknown (ii) MOLECULE TYPE:
            (A) DESCRIPTION: Amide terminated (xi) SEQUENCE DESCRIPTION: SEQ ID NO:22:

Lys Val Gln Pro Tyr Tyr Ser Ser Tyr Tyr
 1               5                  10

(2) INFORMATION FOR SEQ ID NO:23:

(i) SEQUENCE CHARACTERISTICS:
        (A) LENGTH: 15 amino acid residues
        (B) TYPE: amino acid
        (C) STRANDEDNESS:
        (D) TOPOLOGY: unknown (ii) MOLECULE TYPE:
        (A) DESCRIPTION: Amide terminated (xi) SEQUENCE DESCRIPTION: SEQ ID NO:23:

```
Glu Tyr Leu Asn Ser Ile Leu Ser Tyr Ser Pro Ser Tyr Tyr Trp
 1               5                  10                  15
```

(2) INFORMATION FOR SEQ ID NO:24:

(i) SEQUENCE CHARACTERISTICS:
        (A) LENGTH: 15 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 3
        (D) OTHER INFORMATION: cysteine forms disulfide bond
            with cysteine at position 13

(xi) SEQUENCE DESCRIPTION: SEQ ID NO:24:

```
Asp Tyr Cys Asn Lys Val Leu Pro Tyr Tyr Ser Ser Cys Tyr Val
 1               5                  10                  15
```

(2) INFORMATION FOR SEQ ID NO:25:

(i) SEQUENCE CHARACTERISTICS:
        (A) LENGTH: 14 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 2
        (D) OTHER INFORMATION: cysteine forms disulfide bond
            with cysteine at position 12

(xi) SEQUENCE DESCRIPTION: SEQ ID NO:25:

```
Tyr Cys Asn Lys Val Leu Pro Tyr Tyr Ser Ser Cys Tyr Val
 1               5                  10
```

(2) INFORMATION FOR SEQ ID NO:26:

(i) SEQUENCE CHARACTERISTICS:
        (A) LENGTH: 14 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 3
        (D) OTHER INFORMATION: cysteine forms disulfide bond
            with cysteine at position 13

(xi) SEQUENCE DESCRIPTION: SEQ ID NO:26:

Asp Tyr Cys Asn Lys Val Leu Pro Tyr Tyr Ser Ser Cys Tyr
 1               5                  10

(2) INFORMATION FOR SEQ ID NO:27:

(i) SEQUENCE CHARACTERISTICS:
        (A) LENGTH: 13 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 3
        (D) OTHER INFORMATION: cysteine forms disulfide bond
            with cysteine at position 13

(xi) SEQUENCE DESCRIPTION: SEQ ID NO:27:

Asp Tyr Cys Asn Lys Val Leu Pro Tyr Tyr Ser Ser Cys
 1               5                  10

(2) INFORMATION FOR SEQ ID NO:28:

(i) SEQUENCE CHARACTERISTICS:
        (A) LENGTH: 13 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 2
        (D) OTHER INFORMATION: cysteine forms disulfide bond
            with cysteine at position 12

(xi) SEQUENCE DESCRIPTION: SEQ ID NO:28:

Tyr Cys Asn Lys Val Leu Pro Tyr Tyr Ser Ser Cys Tyr
 1               5                  10

(2) INFORMATION FOR SEQ ID NO:29:

(i) SEQUENCE CHARACTERISTICS:
        (A) LENGTH: 13 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 1
        (D) OTHER INFORMATION: cysteine forms disulfide bond
            with cysteine at position 11

(xi) SEQUENCE DESCRIPTION: SEQ ID NO:29:

Cys Asn Lys Val Leu Pro Tyr Tyr Ser Ser Cys Tyr Val
 1               5                  10

(2) INFORMATION FOR SEQ ID NO:30:

(i) SEQUENCE CHARACTERISTICS:
        (A) LENGTH: 12 amino acid residues
        (B) TYPE: amino acid (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 1
        (D) OTHER INFORMATION: cysteine forms disulfide bond
            with cysteine at position 11

(xi) SEQUENCE DESCRIPTION: SEQ ID NO:30:

Cys Asn Lys Val Leu Pro Tyr Tyr Ser Ser Cys Tyr
1               5                   10

(2) INFORMATION FOR SEQ ID NO:31:

(i) SEQUENCE CHARACTERISTICS:
        (A) LENGTH: 11 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 1
        (D) OTHER INFORMATION: cysteine forms disulfide bond
            with cysteine at position 11

(xi) SEQUENCE DESCRIPTION: SEQ ID NO:31:

Cys Asn Lys Val Leu Pro Tyr Tyr Ser Ser Cys
1               5                   10

(2) INFORMATION FOR SEQ ID NO:32:

(i) SEQUENCE CHARACTERISTICS:
        (A) LENGTH: 15 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 7
        (D) OTHER INFORMATION: cysteine forms disulfide bond
            with cysteine at position 12

(xi) SEQUENCE DESCRIPTION: SEQ ID NO:32:

Asp Tyr Leu Asn Lys Val Cys Pro Tyr Tyr Ser Cys Tyr Tyr Val
1               5                   10                  15

(2) INFORMATION FOR SEQ ID NO:33:

(i) SEQUENCE CHARACTERISTICS:
        (A) LENGTH: 14 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 6
        (D) OTHER INFORMATION: cysteine forms disulfide bond
            with cysteine at position 11

(xi) SEQUENCE DESCRIPTION: SEQ ID NO:33:

Tyr Leu Asn Lys Val Cys Pro Tyr Tyr Ser Cys Tyr Tyr Val
 1               5                  10

(2) INFORMATION FOR SEQ ID NO:34:

(i) SEQUENCE CHARACTERISTICS:
             (A) LENGTH: 13 amino acid residues
             (B) TYPE: amino acid
             (C) STRANDEDNESS:
             (D) TOPOLOGY: unknown (ii) MOLECULE TYPE:
             (A) DESCRIPTION: Amide terminated (ix) FEATURE:
             (A) NAME/KEY: Modified-site
             (B) LOCATION: 5
             (D) OTHER INFORMATION: cysteine forms disulfide bond
                 with cysteine at position 10

(xi) SEQUENCE DESCRIPTION: SEQ ID NO:34:

Leu Asn Lys Val Cys Pro Tyr Tyr Ser Cys Tyr Tyr Val
 1               5                  10

(2) INFORMATION FOR SEQ ID NO:35:

(i) SEQUENCE CHARACTERISTICS:
             (A) LENGTH: 12 amino acid residues
             (B) TYPE: amino acid
             (C) STRANDEDNESS:
             (D) TOPOLOGY: unknown (ii) MOLECULE TYPE:
             (A) DESCRIPTION: Amide terminated (ix) FEATURE:
             (A) NAME/KEY: Modified-site
             (B) LOCATION: 4
             (D) OTHER INFORMATION: cysteine forms disulfide bond
                 with cysteine at position 9

(xi) SEQUENCE DESCRIPTION: SEQ ID NO:35:

Asn Lys Val Cys Pro Tyr Tyr Ser Cys Tyr Tyr Val
 1               5                  10

(2) INFORMATION FOR SEQ ID NO:36:

(i) SEQUENCE CHARACTERISTICS:
             (A) LENGTH: 11 amino acid residues
             (B) TYPE: amino acid
             (C) STRANDEDNESS:
             (D) TOPOLOGY: unknown (ii) MOLECULE TYPE:
             (A) DESCRIPTION: Amide terminated (ix) FEATURE:
             (A) NAME/KEY: Modified-site
             (B) LOCATION: 3
             (D) OTHER INFORMATION: cysteine forms disulfide bond
                 with cysteine at position 8

(xi) SEQUENCE DESCRIPTION: SEQ ID NO:36:

Lys Val Cys Pro Tyr Tyr Ser Cys Tyr Tyr Val
 1               5                  10

(2) INFORMATION FOR SEQ ID NO:37:

(i) SEQUENCE CHARACTERISTICS:
             (A) LENGTH: 14 amino acid residues

```
            (B) TYPE: amino acid
            (C) STRANDEDNESS:
            (D) TOPOLOGY: unknown (ii) MOLECULE TYPE:
            (A) DESCRIPTION: Amide terminated (ix) FEATURE:
            (A) NAME/KEY: Modified-site
            (B) LOCATION: 7
            (D) OTHER INFORMATION: cysteine forms disulfide bond
                with cysteine at position 12

(xi) SEQUENCE DESCRIPTION: SEQ ID NO:37:

Asp Tyr Leu Asn Lys Val Cys Pro Tyr Tyr Ser Cys Tyr Tyr
 1               5                  10

(2) INFORMATION FOR SEQ ID NO:38:

(i) SEQUENCE CHARACTERISTICS:
            (A) LENGTH: 13 amino acid residues
            (B) TYPE: amino acid
            (C) STRANDEDNESS:
            (D) TOPOLOGY: unknown (ii) MOLECULE TYPE:
            (A) DESCRIPTION: Amide terminated (ix) FEATURE:
            (A) NAME/KEY: Modified-site
            (B) LOCATION: 7
            (D) OTHER INFORMATION: cysteine forms disulfide bond
                with cysteine at position 12

(xi) SEQUENCE DESCRIPTION: SEQ ID NO:38:

Asp Tyr Leu Asn Lys Val Cys Pro Tyr Tyr Ser Cys Tyr
 1               5                  10

(2) INFORMATION FOR SEQ ID NO:39:

(i) SEQUENCE CHARACTERISTICS:
            (A) LENGTH: 12 amino acid residues
            (B) TYPE: amino acid
            (C) STRANDEDNESS:
            (D) TOPOLOGY: unknown (ii) MOLECULE TYPE:
            (A) DESCRIPTION: Amide terminated (ix) FEATURE:
            (A) NAME/KEY: Modified-site
            (B) LOCATION: 7
            (D) OTHER INFORMATION: cysteine forms disulfide bond
                with cysteine at position 12

(xi) SEQUENCE DESCRIPTION: SEQ ID NO:39:

Asp Tyr Leu Asn Lys Val Cys Pro Tyr Tyr Ser Cys
 1               5                  10

(2) INFORMATION FOR SEQ ID NO:40:

(i) SEQUENCE CHARACTERISTICS:
            (A) LENGTH: 13 amino acid residues
            (B) TYPE: amino acid
            (C) STRANDEDNESS:
            (D) TOPOLOGY: unknown (ii) MOLECULE TYPE:
            (A) DESCRIPTION: Amide terminated (ix) FEATURE:
            (A) NAME/KEY: Modified-site
            (B) LOCATION: 6
            (D) OTHER INFORMATION: cysteine forms disulfide bond
```

```
                  with cysteine at position 11

(xi) SEQUENCE DESCRIPTION: SEQ ID NO:40:

Tyr Leu Asn Lys Val Cys Pro Tyr Tyr Ser Cys Tyr Tyr
 1               5                  10

(2) INFORMATION FOR SEQ ID NO:41:

(i) SEQUENCE CHARACTERISTICS:
        (A) LENGTH: 12 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 5
        (D) OTHER INFORMATION: cysteine forms disulfide bond
             with cysteine at position 10

(xi) SEQUENCE DESCRIPTION: SEQ ID NO:41:

Leu Asn Lys Val Cys Pro Tyr Tyr Ser Cys Tyr Tyr
 1             5                  10

(2) INFORMATION FOR SEQ ID NO:42:

(i) SEQUENCE CHARACTERISTICS:
        (A) LENGTH: 11 amino acid residues
        (B) TYPE: amino acid
        (C) STRANDEDNESS:
        (D) TOPOLOGY: unknown (ii) MOLECULE TYPE:
        (A) DESCRIPTION: Amide terminated (ix) FEATURE:
        (A) NAME/KEY: Modified-site
        (B) LOCATION: 5
        (D) OTHER INFORMATION: cysteine forms disulfide bond
             with cysteine at position 10

(xi) SEQUENCE DESCRIPTION: SEQ ID NO:42:

Leu Asn Lys Val Cys Pro Tyr Tyr Ser Cys Tyr
 1             5                  10
```